United States Patent
Kobayashi

(10) Patent No.: US 12,310,425 B2
(45) Date of Patent: May 27, 2025

(54) SKIN PROTECTION SHEET

(71) Applicant: Yasunari Kobayashi, Nagano (JP)

(72) Inventor: Yasunari Kobayashi, Nagano (JP)

(\*) Notice: Subject to any disclaimer, the term of this patent is extended or adjusted under 35 U.S.C. 154(b) by 814 days.

(21) Appl. No.: 17/260,433

(22) PCT Filed: Jul. 17, 2018

(86) PCT No.: PCT/JP2018/026721
§ 371 (c)(1),
(2) Date: Jan. 14, 2021

(87) PCT Pub. No.: WO2020/016930
PCT Pub. Date: Jan. 23, 2020

(65) Prior Publication Data
US 2021/0289849 A1     Sep. 23, 2021

(51) Int. Cl.
*A41B 9/12* (2006.01)
*A61F 13/00* (2024.01)
*A61F 13/01* (2024.01)

(52) U.S. Cl.
CPC .......... *A41B 9/12* (2013.01); *A61F 13/01029* (2024.01); *A61F 13/01038* (2024.01);
(Continued)

(58) Field of Classification Search
CPC ... A41B 9/12; A41B 2400/72; A41B 2500/30; A61F 13/00029; A61F 2013/00272;
(Continued)

(56) References Cited

U.S. PATENT DOCUMENTS 3,816,227 A \* 6/1974 Schaar ................. A61F 13/539
                                                     156/196
5,647,842 A \* 7/1997 Kininmonth ............. D02G 3/38
                                                     602/76
(Continued)

FOREIGN PATENT DOCUMENTS

DE    102014209591 A1 \* 11/2015 ....... A61F 13/00029
JP           3-27234 U      3/1991
(Continued)

OTHER PUBLICATIONS

Tadao Kawamori—Published Unexamined Application of JPH 105271A (Year: 1998).\*

(Continued)

*Primary Examiner* — Alireza Nia
*Assistant Examiner* — Andrew Jun-Wai Mok
(74) *Attorney, Agent, or Firm* — Birch, Stewart, Kolasch & Birch, LLP

(57) ABSTRACT

When configuring a skin protection sheet covering the skin disease site (including a potential skin disease site, hereinafter the same) of the user by affixing it to the inside surface of the undergarment of the user, a protective sheet main part configured in a gathered shape is provided by forming three-layered surface parts respectively formed by two foldbacks crossing in a predetermined direction at a plurality of positions in a predetermined direction, of a sheet material formed of a nonwoven fabric material, and by providing suture parts sutured in the predetermined direction by a thread material at a predetermined spacing in a direction intersecting the predetermined direction, and one, two, or more sheet affixation parts are provided on one surface of the protective sheet main part for making the protective sheet main part attachable to and removable from the inside surface of an undergarment.

13 Claims, 4 Drawing Sheets

(52) U.S. Cl.
CPC ....... *A41B 2400/72* (2013.01); *A41B 2500/30* (2013.01); *A61F 2013/00272* (2013.01)

(58) Field of Classification Search
CPC .. A61F 2013/00404; A61F 2013/15024; A61F 2013/51361
See application file for complete search history.

(56) References Cited

U.S. PATENT DOCUMENTS

| | | | |
|---|---|---|---|
| 6,067,987 A * | 5/2000 | Scheinberg | A61F 13/0206 128/889 |
| 2003/0082970 A1 | 5/2003 | Moberg-Alehammar et al. | |
| 2011/0208149 A1 * | 8/2011 | Vastag | A61F 13/49011 604/385.16 |

FOREIGN PATENT DOCUMENTS

| | | | |
|---|---|---|---|
| JP | 10-5271 A | | 1/1998 |
| JP | H-105271 A | * | 1/1998 |
| JP | 2007-97911 A | | 4/2007 |
| JP | 2015231424 A | * | 12/2015 |
| JP | 2016-101525 A | | 6/2016 |
| JP | 2017-23662 A | | 2/2017 |
| JP | 6362437 B2 | * | 7/2018 |

OTHER PUBLICATIONS

Kawamori T—Jan. 13, 1998.*
Gross H—Nov. 26, 2015.*
International Continence Society, Skin Damage from Incontinence, Feb. 27, 2015.*
Kobayashi, Care Diaper Auxiliary Sheet, Dec. 24, 2015.*
Jul. 25, 2018, Kobayashi, Auxiliary sheet for nursing diapers.*
International Search Report, issued in PCT/JP2018/026721, dated Aug. 14, 2018.

* cited by examiner

SKIN PROTECTION SHEET

TECHNICAL FIELD

The present invention relates to a skin protection sheet for protecting a user's skin disease site or potential skin disease site by affixing it to the inside surface of his/her undergarment.

BACKGROUND ART

Generally, when a person sleeps on his/her back for an extended period due to illness or injury, skin disease due to so-called bedsores is likely to occur, and when an undergarment is in close contact with the skin, a skin disease such as miliaria due to being so-called sweaty is expected to occur. Therefore, it is also useful to provide a medium with a certain auxiliary effect for treating or preventing a skin disease between the inside surface of the undergarment and the skin disease site. A medium for this purpose has already been proposed.

Conventionally, as such a medium, a mat for preventing bedsores disclosed in Patent Document 1 is known. The mat for preventing bedsores has a shape in which a web or a cloth containing a far-infrared radiation fiber can be brought into contact with the waist and the buttocks, specifically, a shape in which a central lower part with which a coccyx is brought into contact is cut out, and can be affixed to the inside of the back surface of a diaper cover or a pair of underpants.

PRIOR ART PUBLICATIONS

Patent Publications

Patent Literature: JP H03-27234U

DISCLOSURE OF THE INVENTION

Problem to be Solved by the Invention

However, the above-described conventional mat for preventing bedsores has the following problems.

First, since the mat is composed of a web or cloth containing far-infrared radiation fibers, the total manufacturing cost (initial cost), including the material cost, is likely high.

Since the mat is used in an environment where it is expected to become dirty, such as being affixed to the back of a diaper cover or underpants, it is necessary to replace the mat every time due to hygiene requirements. The running cost is also likely to be high so that the total cost increase cannot be ignored.

Second, since it is a specific treatment medium whose far-infrared ray effect is expected, it is difficult to guarantee the degree of the effect to be expected in the treatment or prevention of various skin diseases, and it has difficulty in versatility, and depending on the skin disease, it is also considered that the symptom may be exacerbated. Moreover, from the viewpoint of ensuring ventilation (non-contact with the skin), sufficient consideration is not always given, and from the perspective of securing comfort (touch feeling) during wearing, adequate care is not necessarily provided.

An object of the present invention is to provide a skin protection sheet that solves such problems existing in the background art.

Means for Solving the Problem

In order to solve the above-described problems, a skin protection sheet 1 according to the present invention is characterized by providing the following: when configuring a skin protection sheet which is affixed to the inside surface Ci of an undergarment C of a user H for protecting a skin disease site (including a potential skin disease site, hereinafter the same) Xw of the user H, forming multi-layered surface parts K of a sheet material S of a nonwoven fabric material, respectively, by folding back a plurality of times intersecting the predetermined direction Fm, at a plurality of positions in the direction Fm, and providing suture parts 5 sutured in the predetermined direction Fm by a thread material 4 at a predetermined spacing in a direction Fs intersecting the predetermined direction Fm, thereby a protective sheet main part 2 configured in a gathered shape and one, two, or more sheet affixation parts 3 are provided on one surface 2r of the protective sheet main part 2 to enable the protective sheet main part 2 to be affixed and removed to the inside surface Ci of an undergarment C.

In this case, according to the preferred embodiment of the present invention, the thread material 4 is composed of one thread member 4a or two thread members 4a and 4b, and at least one thread member 4a can include the rubber thread 4ar. Besides, the skin disease site Xw may include at least a bedsore site in the buttocks Hh. Further, the sheet material S can be used by stacking one or two or more sheets.

Effects of the Invention

According to the skin protection sheet 1 of the present invention having such a configuration, the following remarkable effects are obtained.

(1) A multi-layer surface part K is formed by a plurality of folds intersecting the predetermined direction Fm at a plurality of positions in a predetermined direction Fm, respectively, of sheet material S of nonwoven fabric material, is provided with a protective sheet body 2 formed by suturing in the predetermined direction Fm with a thread material 4, whereby the overall production cost (initial cost) including the material cost can be reduced, and the running cost can be reduced even when it is made disposable, thus achieving a significant overall cost reduction.

(2) Since the protective sheet main part 2 is formed in a gathered shape by a sheet material S using a nonwoven fabric material, an adequate ventilation space is generated between the skin disease site Xw and the inside surface Ci of the undergarment C, and non-contact with the skin can be enhanced. As a result, it is possible to enjoy a certain auxiliary effect for the treatment or prevention of various diseases on the skin surface, and it is possible to enhance the versatility. Besides, the gather mode can further improve the comfort (feeling of touch) when wearing it.

(3) If the thread material 4 is composed of one thread member 4a or two thread members 4a and 4b, and the rubber thread 4ar is included in at least one thread member 4a according to the preferred embodiment, necessary elasticity can be secured, and therefore, even when the skin disease site Xw occurs at the bent portion or the like of the user H, the user can comfortably use the product without inhibiting the bending motion.

(4) If the skin disease site Xw includes at least the area where the bedsore of the buttocks Hh occurs according to the preferred embodiment, the skin disease site Xw can enjoy an additional benefit relating to highly effective treatment or prevention in place of the moisturizing therapy which has been mainly performed for bedsore.

(5) Since the number of sheet materials S can be arbitrarily selected, and one, two, or more sheets can be stacked and used according to the preferred embodiment, it is possible to easily adjust the degree of comfort (touch feeling) at the time of wearing and the degree of cost. It is also possible to easily cope with the diversification of product grades and the like.

DESCRIPTION OF REFERENCE NUMERALS

1: skin protection sheet, 2: protective sheet main part, 2r: one surface (non-contact surface) of protective sheet main part, 3: sheet affixation part, 4: thread material, 4a: thread member, 4b: thread member, 4ar: rubber thread, 5: suture part, H: user, Hh: Buttocks, C: undergarment, Ci: inside surface of undergarment, Xw: skin disease site, S: sheet material formed of nonwoven fabric material, Fm: predetermined direction, Fs: direction intersecting the predetermined direction, K: multi-layered surface parts (three-layered surface part)

BEST MODE FOR CARRYING OUT THE INVENTION

Next, the best embodiment according to the present invention will be described in detail with reference to the drawings.

First, the entire structure of the skin protection sheet 1 according to the present embodiment, including the used members and the manufacturing methods, will be described with reference to FIGS. 1-6.

Figure 3:
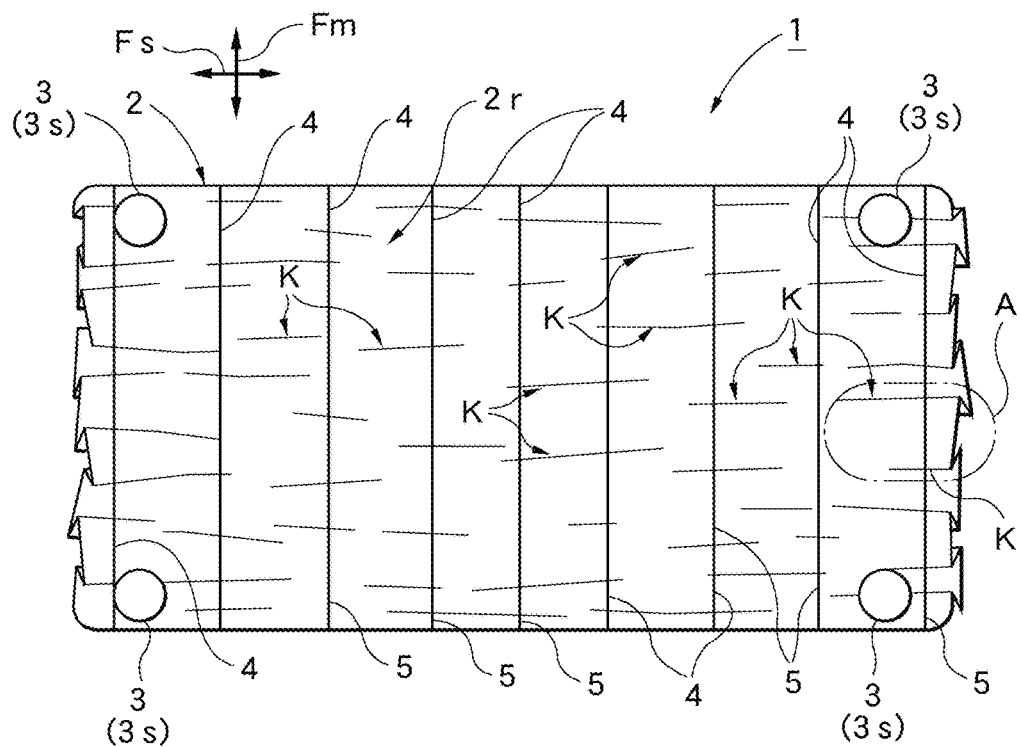
FIG. 3 is a rear view of the skin protection sheet.

The illustrated skin protection sheet 1 is intended to treat or prevent bedsore in the buttocks Hh of the user H. As shown in FIG. 3, a basic configuration comprises a protective sheet main part 2 having a rectangular shape being horizontally long as a whole, and a sheet affixation part 3 for attaching and removing the protective sheet main part 2 to/from the inside surface Ci of the undergarment C of the user H.

The protective sheet main part 2 is configured (produced) in a gathered shape by forming three-layered surface parts K of a sheet material S composed of nonwoven fabric material at a plurality of predetermined positions in a predetermined direction Fm, and being folded back two times and intersecting the predetermined direction Fm, respectively, and providing suture parts 5 stitched to the predetermined direction Fm by a thread material 4, at a predetermined spacing in a direction Fs intersecting the predetermined direction Fm.

The nonwoven fabric material used for the sheet material S is not limited to specific material, but a nonwoven fabric material excellent in low cost and suitable in touch feeling is desirable. As an example, a thermally bonded nonwoven fabric (trade name) manufactured by Rengo Nonwoven Products Co., Ltd. can be used. This product is made by processing a short plastic fiber as raw cotton into a nonwoven fabric by non-binder and heat fusion and has the advantage of being sanitary and excellent in flexibility.

Figure 5:
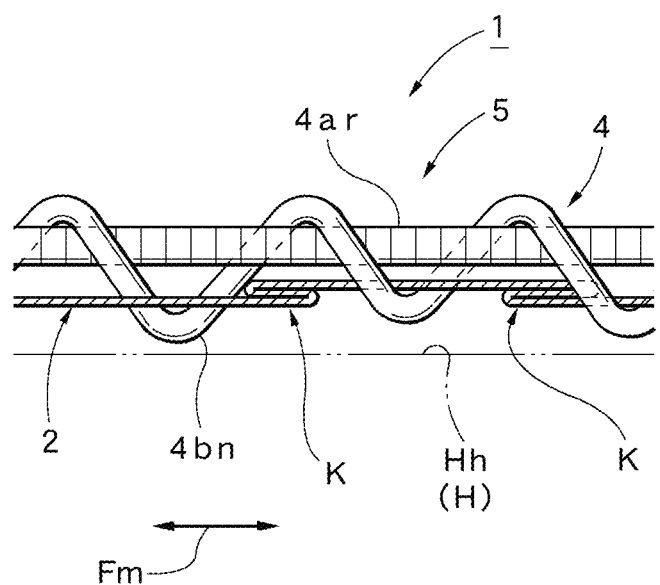
FIG. 5 is an enlarged side view of a part of a cross-section of a suture part in the skin protection sheet.
Figure 6:
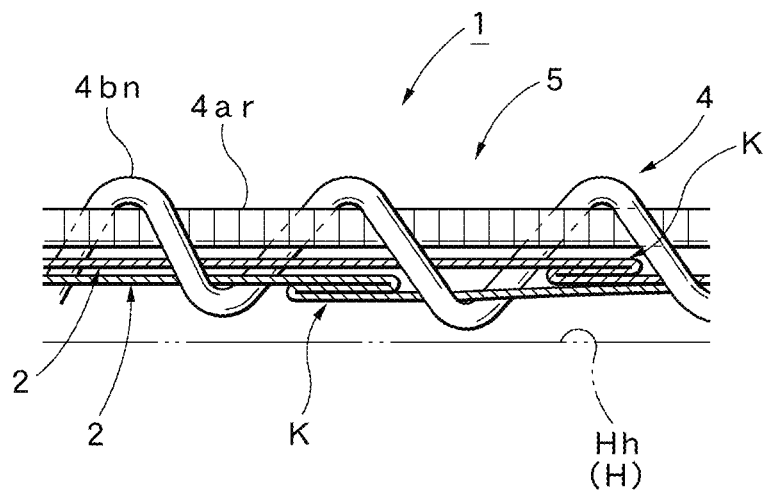
FIG. 6 is an enlarged side view of a part of a cross-section of a suture part according to a modification example of the skin protection sheet.

As shown in FIG. 5, the number of sheets S to be used constituting the protective sheet main part 2 may be one sheet, or two stacked sheets S, as shown in FIG. 6. If necessary, three or more sheets may be stacked. In this way, the number of sheets S to be used can be arbitrarily selected. Therefore, it is possible to easily adjust the degree of comfort (touch feeling) at the time of wearing and the degree of cost performance, and it is also possible to easily cope with the diversification of product grades and the like.

On the other hand, two thread members 4a and 4b are used for the suture parts 5. Specifically, a rubber thread 4ar arranged on the skin non-contact surface 2r of the protective sheet main body 2 which does not contact the skin of the user H and a natural fiber thread 4bn such as a cotton thread by which the rubber thread 4ar is sutured to the protective sheet main body 2 are used. Therefore, the combination of the rubber thread 4ar (thread member 4a) and the natural fiber thread 4bn (thread member 4b) is the thread material 4 used in this embodiment.

Figure 4:
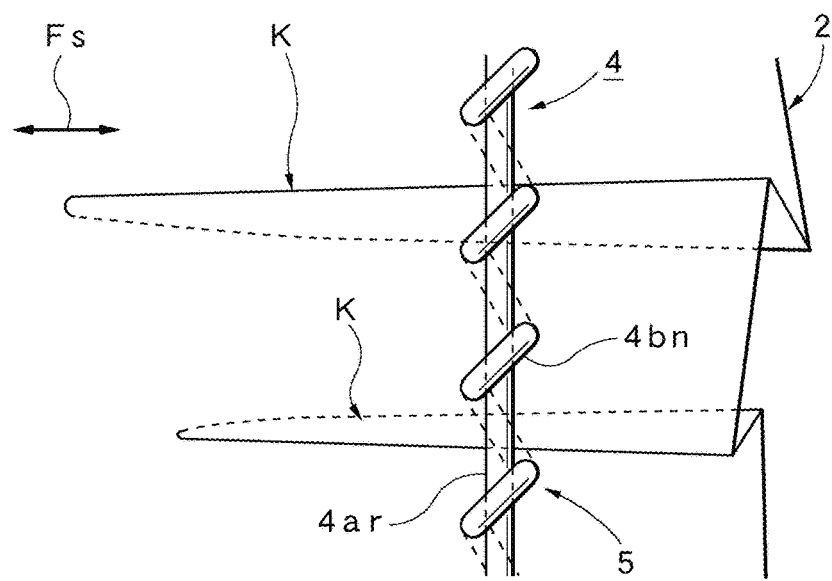
FIG. 4 is an enlarged view of an enclosure line A in FIG. 3 of the skin protection sheet.

When suturing the thread material 4, one of the rubber thread 4ar and the natural fiber thread 4bn is used as the upper thread and the other as the lower thread, which can be sutured by a suturing machine (not shown). Therefore, when suturing, first, the rubber thread 4ar and the natural fiber thread 4bn are loaded into the suturing machine. Then, the sheet material S is set in the suturing machine. At a plurality of predetermined positions in a predetermined direction (in the lateral direction in FIG. 3) Fm of the sheet material S, the sheet material S is folded back twice, having folding lines intersecting with the predetermined direction Fm to form three-layered surface parts K at each predetermined position. This state is sutured by a thread material 4. The suturing direction is the predetermined direction Fm, whereby the suture parts 5 are provided at predetermined positions. As seen in FIG. 3, the fold-backs K do not extend an entire length of the sheet material in the first direction but the suture parts 5 extend an entire length of the sheet material in the second direction. At least one of the plurality of fold-backs is spaced from edges of the sheet material. As seen in FIG. 4, at least two of the three-layered surface parts are folded in different directions.

In this case, as shown in FIGS. 4 and 5, the rubber thread 4ar is arranged on the skin non-contact surface 2r of the protective sheet main part 2 (sheet material S), and the natural fiber thread 4bn is exposed on the skin contact surface 2p which is the opposite surface to the non-contact surface 2r. In the illustrated example, nine suture parts 5 are provided at a predetermined spacing in the predetermined direction Fm of the protective sheet main part 2 (see FIG. 3). As a result, the protective sheet main part 2 can be elastically extended and contracted in the direction Fs (the longitudinal direction in FIG. 3) intersecting the predetermined direction Fm by the rubber thread 4 ar. At this time, the length at the time of extension should be set to be approximately 1.5 times the length before the extension (before the extension).

As described above, when the suture part 5 is provided, the thread material 4 comprises two thread members 4a and 4b. If the rubber thread 4ar is included in at least one thread member 4a, the necessary elasticity can be secured. Therefore, there is an advantage that comfortable use is possible without inhibiting the bending motion even when the skin disease site Xw occurs at the bent portion or the like of the user H.

In particular, as a preferred embodiment, using the rubber thread 4ar for the thread member 4a arranged on the non-contact surface 2r of the protective sheet main part 2, and using the natural fiber thread 4bn for the thread member 4b for suturing the rubber thread 4ar to the protective sheet main part 2 enable rubber thread 4ar to avoid directly hitting the skin of the user H while securing the necessary elasticity. Although a case is illustrated where two thread members 4a and 4b are used as the thread member 4, only one thread member 4a may be used, and in this case, a rubber thread 4ar may be used as one thread member 4a.

If the suture part 5 is provided, the protective sheet main part 2 (sheet material S) may be pressed in a direction perpendicular to the plane by sandwiching the protective sheet main part 2 (sheet material S) between a pair of flat plates, as necessary. As a result, the slack portion of the sheet material S is crushed, and the folded part is in a crushed state, as shown in FIG. 5. That is, the entire structure is formed into a gathered shape and a sheet shape.

Figure 1:
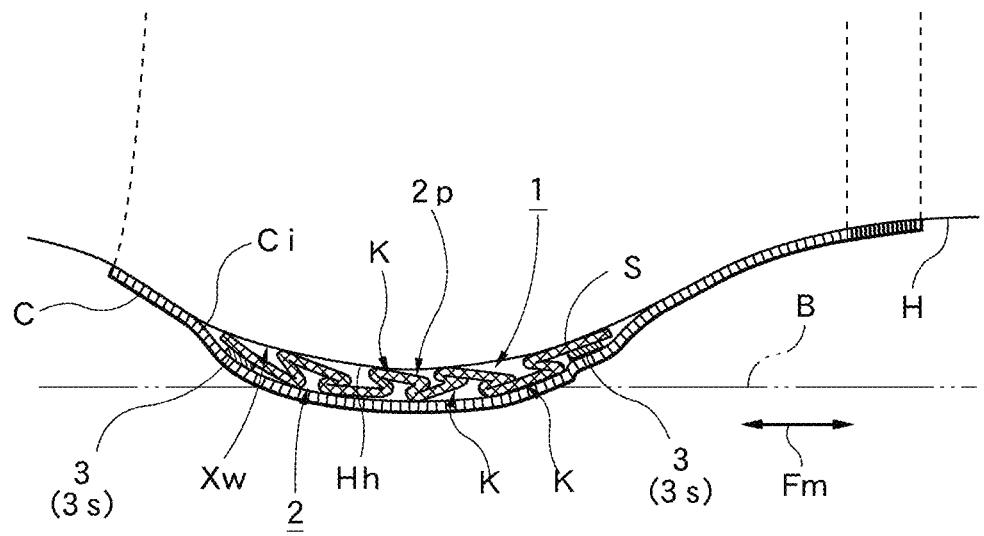
FIG. 1 is a side cross-sectional view showing a state in which a skin protection sheet according to the preferred embodiment of the present invention is used for the buttocks.

On the other hand, the sheet affixation part 3 has a function of attaching and removing the protective sheet main part 2 to/from the inside surface Ci of the undergarment C. Therefore, as shown in FIGS. 1 and 3, a circular double-sided adhesive tape 3s can be affixed in the vicinity of four corners of the skin non-contact surface 2r of the protective sheet main part 2. This double-sided adhesive tape 3s is formed to have a diameter of approximately 20 [mm], and a release paper remains to be affixed to each double-sided adhesive tape 3s until it is used.

As described above, the skin protection sheet 1 according to the present embodiment is basically configured as follows: three-layered surface parts K are made respectively by two fold-backs that cross in a predetermined direction Fm at a plurality of positions in the predetermined direction Fm of the sheet material S formed of the nonwoven fabric material. The protective sheet main part 2 formed into a gathered shape by providing suture parts 5 sutured in a predetermined direction Fm using a thread material 4 at a predetermined spacing, in a direction Fs intersecting the predetermined direction Fm, and one, two, or more sheet affixation parts 3 which make the protective sheet main part 2 attachable to and removable from the inside surface Ci of the undergarment C on one surface 2r of the protective sheet main part 2 are provided. Therefore, the overall production cost (initial cost), including the material cost, can be reduced, and the running cost can be reduced even in the case of being made disposable so that the overall significant cost reduction can be realized.

Figure 7:
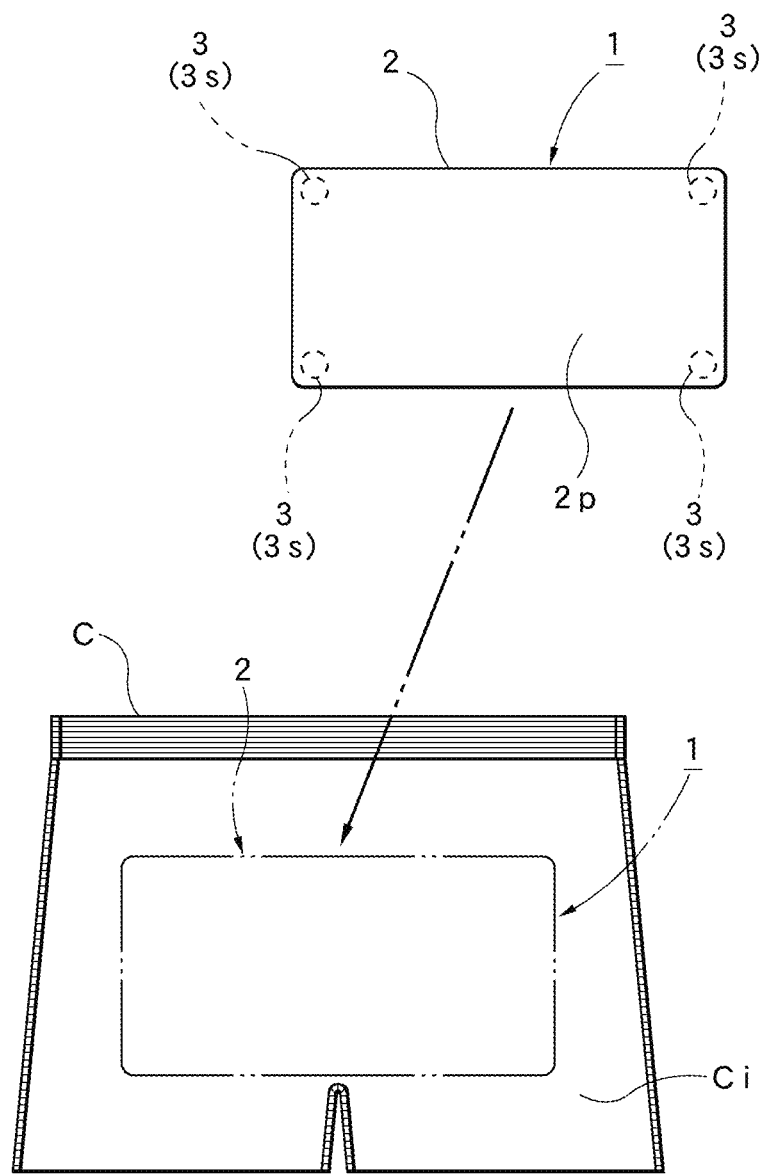
FIG. 7 illustrates how to use the skin protection sheet.

Next, a usage and a function (operation) of the skin protection sheet 1 according to the present embodiment will be described with reference to FIGS. 7-9.

First, when the skin protection sheet 1 is used, it is affixed to the inside surface Ci of the undergarment C of the user H. As shown in FIG. 7, in the present embodiment, underpants illustrate the undergarment C, and the exemplified skin protection sheet 1 is used to treat (or prevent) bedsore occurring in the buttocks Hh of the user H.

Figure 2:
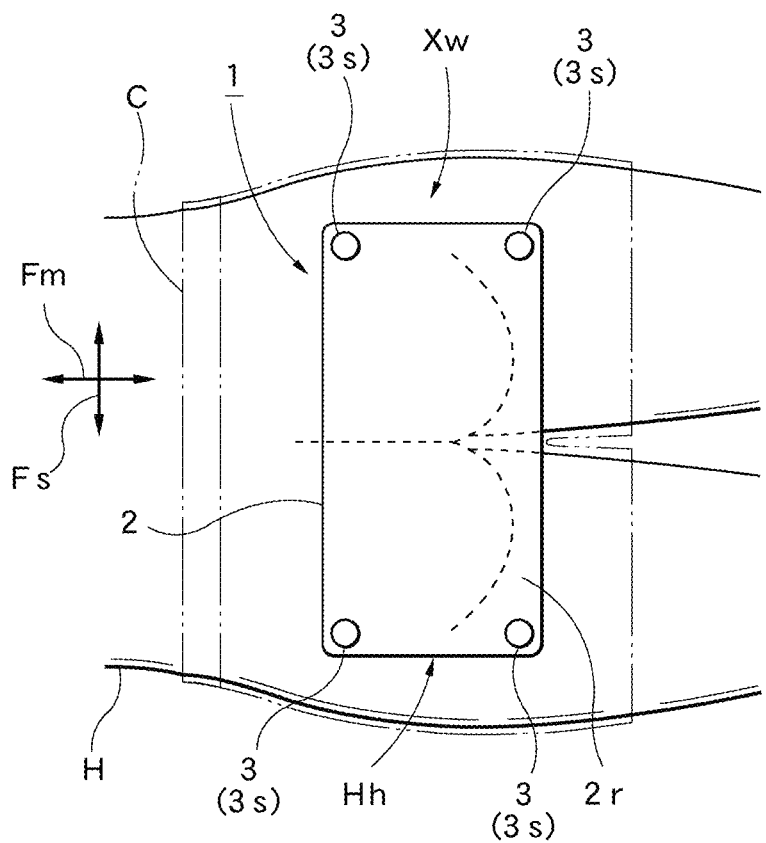
FIG. 2 is a rear view showing a state in which the skin protection sheet is used for the buttocks.

When the skin protection sheet 1 is used, the peeling paper affixed to the double-sided adhesive tapes 3s at four sites in the prepared skin protection sheet 1 is peeled off. Then, as shown by an arrow Fu in FIG. 7, the double-sided adhesive tape 3s is affixed to the inside surface Ci located on the backside of the undergarment C, and the skin protection sheet 1 is fixed. In this case, as shown in FIGS. 1 and 2, the attachment position is selected so that the skin contact surface 2p of the protective sheet main part 2 can cover the buttocks Hh of the user H, that is, the skin disease site Xw where bedsores have occurred. Thus, the attachment (mounting) of the skin protection sheet 1 is completed, and the skin protection sheet 1 can be mounted very easily in a short time.

On the other hand, when the user H attaches the undergarment C (underpants) having the skin protection sheet 1 affixed thereto to the body following the normal procedure, as shown in FIGS. 1 and 2, the skin contact surface 2p of the protective sheet main part 2 covers the skin disease site Xw where bedsore has occurred in the user H. Therefore, as shown in FIG. 1, even when the user H lies on his/her back on the bed B, or the like, the protective sheet main part 2 is interposed between the skin disease site Xw where bedsore has occurred and the inside surface Ci of the undergarment C.

In this case, since the protective sheet main part 2 is formed in a gathered shape by the sheet material S made of the nonwoven fabric material, a good ventilation space is generated between the skin disease site Xw and the inside surface Ci of the undergarment C, and the non-contact with the skin can be further enhanced. As a result, it is possible to enjoy a certain additional benefit for treating or preventing various diseases on the skin surface. It is possible to enhance the versatility further and further enhance the comfort (touch feeling) at the time of mounting by the gather mode.

A skin condition showed improvement even after six days of skin protection sheet 1. It is considered that the reason for this is that the healing effect against bedsores worked effectively by ensuring ventilation. As described above, including at least the site where the bedsore of the buttocks Hh occurs, the skin disease site Xw can enjoy an additional benefit of highly effective treatment or prevention, which replaces the conventional moisturizing therapy for bedsores.

The best embodiment has been described above in detail. However, such an embodiment is not the limitation of the present invention. This invention allows arbitrary change, addition, or deletion of detailed configuration, shape, material, quantity, method, etc., within the scope of the gist of the present invention.

For example, one sheet material S or two or more sheet materials S may be combined, but a mode of combining one sheet material S (or two or more sheet materials) with a sheet member formed of another material (general paper or the like) is not excluded. Although the natural fiber thread 4bn is used as the thread member 4b is exemplified, other threads such as chemical fiber thread are not excluded. Further, the term "folding back in the way of intersecting the predetermined direction Fm" is a concept including not only intersecting at a right angle but also intersecting at various angles.

On the other hand, as the undergarment C, various kinds of undergarments directly facing the skin disease site Xw of the user H, such as the illustrated underpants, can be applied. Accordingly, a diaper, or the like, is included in the undergarment C to which the present invention is applied. Besides, the skin disease site Xw is exemplified by the bedsore of the buttocks Hh, but it is a concept including various skin conditions requiring protection, i.e., multiple diseases occurring on the skin such as miliaria and wounds on the skin caused by an injury. Besides, a potential skin disease site (Xw) is a concept of a region where a skin disease has not occurred at present but is likely to occur later. Therefore, in this case, skin protection sheet 1 can be used as a preventive measure. It should be noted that the user H mentioned above is a care receiver, but it is also applicable to a general adult who is hospitalized due to injury, or the like, and is sleeping on a bed, or any person who is in a normal state to prevent miliaria or the like.

On the other hand, although the sheet affixation parts 3 are provided at four locations as an example, the sheet affixation parts 3 formed in a tape shape can be provided at two locations at the top and bottom, and the sheet affixation parts 3 formed in a frame shape can suffice with only one place. Therefore, the number of sheet affixation parts 3 is arbitrary. Further, as illustrated in the embodiment, although it is desirable to form the three-layered surface parts K by two fold-backs that cross in a predetermined direction Fm, it is also possible to form the multi-layered surface parts K by a plurality of fold-backs crossing in a predetermined direction Fm, if necessary.

Industrial Applicability

The skin protection sheet according to the present invention can be used in various applications in which a certain assisting effect for treatment or prevention of various skin diseases can be expected by protecting the skin disease site of a user.

The invention claimed is:

1. A skin protection sheet adapted for protecting a skin disease site, including a potential skin disease site, of a user by affixing the skin protection sheet to an inside surface of an undergarment of the user, comprising: at least one sheet formed of non-woven fabric material, each at least one sheet forming a sheet layer and including; side edges spaced from each other in a first direction and end edges spaced from each other in a second direction; multi-layered surface parts respectively formed by a plurality of fold-backs crossing in the first direction at a plurality of positions in the first direction, wherein at least one fold-back of the plurality of fold-backs for a plane of each sheet layer of the at least one sheet, is folded in an opposite direction to an adjacent fold-back of the respective each sheet layer of the at least one sheet in the same plane; a plurality of suture parts sutured in the second direction with a string material; and at least one sheet affixation part for removably attaching a main part of the skin protection sheet to the inside surface of the undergarment, the at least one sheet affixation part being located at one surface of the main part of the skin protection sheet.

2. The skin protection sheet described in claim 1, wherein the string material comprises one thread member or two thread members, with at least one thread member containing a rubber thread.

3. The skin protection sheet described in claim 2, wherein the at least one sheet is a plurality of sheets which are stacked and used.

4. The skin protection sheet described in claim 1, wherein the plurality of fold-backs do not extend an entire length of the at least one sheet in the first direction.

5. The skin protection sheet described in claim 4, wherein the plurality of suture parts extend an entire length of the at least one sheet in the second direction.

6. The skin protection sheet described in claim 1, wherein the multi-layered surface parts are three-layered surface parts.

7. The skin protection sheet described in claim 6, wherein the string material comprises a first rubber thread and a second thread, the second thread made from a cotton material or polymer material, and wherein the rubber thread is only on a non-skin contact surface of the at least one sheet.

8. The skin protection sheet described in claim 6, wherein second thread extends through the three-layered surface parts.

9. The skin protection sheet described in claim 6, wherein at least two of the three-layered surface parts are folded in different directions.

10. The skin protection sheet described in claim 1, wherein the at least one sheet is a plurality of sheets which are stacked and used.

11. The skin protection sheet described in claim 1, wherein the second direction is perpendicular to the first direction.

12. The skin protection sheet described in claim 1, wherein the plurality of suture parts extend across the plurality of fold-backs.

13. The skin protection sheet described in claim 1, wherein opposite ends of at least one of the plurality of fold-backs are spaced from the side edges of the at least one sheet.

* * * * *